US006725726B1

(12) United States Patent
Adolfs et al.

(10) Patent No.: US 6,725,726 B1
(45) Date of Patent: Apr. 27, 2004

(54) PRESSURE DOME FOR CONNECTING A TRANSDUCER WITH A SEALED FLUID SYSTEM

(75) Inventors: Manfred Adolfs, Steinfurt (DE); Raymond Glocker, Münster (DE)

(73) Assignee: Memscap AS, Sloppum (NO)

( * ) Notice: Subject to any disclaimer, the term of this patent is extended or adjusted under 35 U.S.C. 154(b) by 0 days.

(21) Appl. No.: 09/600,825
(22) PCT Filed: Jan. 23, 1999
(86) PCT No.: PCT/EP99/00438
§ 371 (c)(1), (2), (4) Date: Nov. 15, 2000
(87) PCT Pub. No.: WO99/37983
PCT Pub. Date: Jul. 29, 1999

(30) Foreign Application Priority Data

Jan. 24, 1998 (DE) .......................................... 198 02 615

(51) Int. Cl.[7] ................................................. G01L 7/00
(52) U.S. Cl. ....................................................... 73/756
(58) Field of Search .................. 73/756, 706; 600/485, 600/488, 561

(56) References Cited

U.S. PATENT DOCUMENTS

| 4,462,409 A | 7/1984 | Pace et al. |
| 4,562,845 A | 1/1986 | Furst et al. |
| 4,920,972 A | 5/1990 | Frank et al. |
| 5,551,300 A | 9/1996 | Vurek et al. |

FOREIGN PATENT DOCUMENTS

| DE | 35 25 536.6 | 1/1987 |
| DE | 42 19 888.7 | 1/1994 |
| WO | WO 97/39679 | 10/1997 |

OTHER PUBLICATIONS

Buchwalsky, R., "Einschwemmkatheter, Technik, Auswertuny und Praktische Konsequenzen" Beitrage Zur Kardiologie, vol. 29 Erlangen. PerimedFachbuch–Verlagsgesellschaft, 1985 pp. 106–109.
"Disposable Transducer Domes", Specialty Medical Products, Dallas Texas, no date.
"SensoNor 840" Product Brochure, Edition 1/95, SensoNor a.s., Horten, Norway.
PCT/EP99/00438, International Search Report, Form PCT/ISA/210, dated Sep. 7, 1999, in German language and English language translation thereof.
PCT/EP99/00438, International Preliminary Examination Report, Form PCT/IPEA/409, dated May 22, 2000, in German language and English language translation thereof.
Verified English language translation of PCT/EP99/00438.

*Primary Examiner*—Robert Raevis
(74) *Attorney, Agent, or Firm*—Paul A. Beck & Assoc.

(57) ABSTRACT

The invention relates to a pressure dome for connecting a transducer with a fluid system comprising an inlet channel and an outlet flow as well as a measuring chamber in which a fluid is able to circulate and which has a measuring membrane. To improve fluid irculation and simplify handling, the measuring chamber ceiling is configured in the shape of a calotte and the pressure dome is removably coupled to the transducer housing by means of a snap connection.

7 Claims, 3 Drawing Sheets

PRESSURE DOME FOR CONNECTING A TRANSDUCER WITH A SEALED FLUID SYSTEM

BACKGROUND OF THE INVENTION

1. Field of the Invention

The invention relates to a connecting element for connecting a transducer to a sealed fluid system, comprising at least one inlet channel, at least one outlet channel and a measuring chamber connected at least to at least one inlet channel and at least one outlet channel in such a way as to allow a flow to pass through, the measuring chamber being formed in a housing and part of the wall of the measuring chamber being formed by a membrane which is significantly more compliant than the remaining part of the wall of the measuring chamber.

Such connecting elements are known in medical technology by the colloquial term "dome" or "pressure dome", which originates from the dome-shaped design of the measuring chamber. They serve the purpose of permitting the measurement of pressures in fluids during the examination and treatment of people and animals, preferably by means of electronic equipment.

2. Description of the Prior Art

For pressure monitoring during the flushing of body cavities, in DE 42 19 888 A1, for example, there is described a flow pressure transducer with such a connecting element, which is designed for a large volume throughput in accordance with the intended area of use.

For monitoring hemodynamic parameters of a patient, in particular intensive-care patients, it is customary nowadays in addition to the recording of an ECG also to record the invasive pressures into the [sic] patient monitoring, that is to say keeping a check on the state of the vital bodily functions of the patient. Depending on the degree of monitoring, between one and four pressures (arterial, pulmonary-arterial, LAP and venous) are measured.

For this purpose, a catheter with an integrated monitoring set is used. The positioning of the end opening of the catheter defines the measuring point in the patient's body. A monitoring set refers to a compilation of those parts which establish the connections between the patient and the so-called monitor and, usually for reasons of hygiene, are intended for once-only use. A monitor refers to the electronic monitoring and recording system with which the corresponding measured data are evaluated and displayed, and which in case of need emits corresponding alarm signals if measured data leave prescribed set ranges.

A general description of this, relating to the example of examination by a flow-directed catheter, is found in Buchwalsky, Rainer: Einschwemmkatheter: Technik, Auswertung u. prakti. Konsequenzen [flow-directed catheters: technology, evaluation and practical consequences] (Beiträge zur Kardiologie [articles on cardiology], Vol. 29); Erlangen: perimed Fachbuch-Verlagsgesellschaft, 1985, pages 106–109.

The monitoring set to be fastened to the catheter comprises an unventilated infusion apparatus for feeding infusion solutions to the patient, a flushing system, which ensures a continuous flushing rate of customarily 3 ml/h at the catheter tip to avoid occlusion being caused by thrombi, if appropriate with a quick flushing function for special cases, and a pressure dome. The pressure dome transmits the pressure signal via its flexible membrane to a reusable transducer (pressure sensor). Such a pressure dome has in the past been fastened on such a transducer by a screw or bayonet connection (see in this respect DE 42 19 888 A1, column 3, lines 28 to 30).

Examples of such pressure domes are to be found on information sheet "Disposable Transducer Domes" of the company SMP Specialty Medical Products, Dallas, Tex., US, with reference to the models 078 to 082. A typical transducer (pressure sensor) is described, for example, in a leaflet of the company SensoNor a.s, Horten, NO, Edition 1/95, on the product SensoNor 840.

Further elements of a monitoring set are the pressure hoses (marked in color) and possibly a three-way cock, to allow medicaments to be fed in, or a blood removal system for taking blood for further investigations.

A special problem is that of venting the parts of the monitoring set in connection with the blood system. The problems involved in venting such systems are generally known to the users. During the filling of the system (usually with physiological saline solution) air bubbles become trapped particularly easily in the dome, i.e. in its dome-like measuring chamber above the membrane. On account of the great elasticity inherent in gases, by contrast with the virtually incompressible fluids, the air bubbles trapped there represent a barrier in the transmission of pressure frequencies of more than a few Hertz. This has the effect of significantly falsifying the transmission of the change in pressure to the membrane, and consequently to the transducer lying thereunder, and as a result the representation of the pressure curves on the monitor.

A connecting element of the type mentioned at the beginning is known from prior public use by SMP Specialty Medical Products, Dallas, Tex., US, under the type designation 081. This "dome" is intended to fit the Hewlett Packard 1290 Quartz transducer and allow itself to be fastened on the latter by means of a bayonet connection. Lockable Luer-lock connections with a loose threaded part, or with an external full thread, as are specified for example in DIN 13 090 Part 2, serve for connecting the inlet channel and outlet channel to the hoses of a monitoring set.

The known connecting element is produced from a crystal-clear plastic. The measuring chamber of this connecting element is very large and has, in particular, a large diameter of approximately 23 mm. In this case, the ceiling of the measuring chamber is at the same time the upper side of the housing. This ceiling and upper side of the housing is formed in a plane-convex manner as a magnifying lens. This is intended to achieve the effect that even small bubbles in the measuring chamber are detected as reliably as possible by the medical care personnel.

Disposable transducers which contain the pressure-measuring sensor in a flow housing are therefore designed in the form of a simple tube in the flow chamber in order to avoid this very trapping of air bubbles. However, they have the disadvantage that the valuable electronics are integrated in the disposable article and therefore are thrown away each time the monitoring set is changed and have to be disposed of along with it. To comply with hygiene requirements, such an exchange must take place at the latest every second day. This entails not only the disadvantage that the still serviceable electronics are replaced with every change, accompanied by corresponding costs, but also that the presence of electronic components requires additional special, and consequently cost-intensive, treatment as electronic scrap during disposable.

For this reason, dome systems which can be used repeatedly are becoming more popular, at least in Europe. The valuable electronics, in particular the pressure sensor, are located in a special housing. Such a part is usually referred to as the transducer. One or more transducers are integrated in a special retaining plate. The retaining plate is fastened, for example on an infusion stand, by means of a clamping or screwing device. The measured pressure data are transmitted from the transducers in the retaining plate to the monitor via one or more cables.

When in the past it was necessary to mount a twin or even triple monitoring set on a number of transducers with the screw or bayonet connection usually encountered in the case of repeatedly reusable transducers, the turning movements necessary for this were possible to a restricted extend only in the case of the first transducer. When mounting on the second transducer, the presence of the structure mounted on the first transducer was already a hindrance. Mounting a second dome onto the second transducer was not possible without removing the transducer from a common retaining plate.

This complicated handling is not only troublesome, it also represents an absolute obstacle to designing retaining plates with permanently fitted transducers and rear-side cabling.

This problem is also not solved by a connecting element of the type mentioned at the beginning, such as that described in DE 35 25 536 A1. To avoid damage, in particular to the membrane of the connecting element, a fastening in which it is not necessary for the connecting element and transducer to be turned in relation to one another is proposed there. For this purpose, additional fastening elements, such as pivotably mounted clamps or clip-like elements, are to be provided at two points of the circumference of the housing of the connecting element.

It is proposed there to allow these fastening elements or continuations to protrude downward beyond the membrane for the handling of the fastening elements. This is intended to make it possible to check visually that locking of the fastening element provided has also been carried out. Furthermore, this is intended to simplify handling when the connecting element is removed from the transducer. However, it practically rules out a combination with transducers fastened in retaining plates.

SUMMARY OF THE INVENTION

The invention is therefore based on the object of providing a connecting element of the type mentioned at the beginning which has improved properties with regard to its application-related reliability on the one hand and its handling on the other hand.

This object is achieved according to the invention by a connecting element of the type mentioned at the beginning in which the measuring chamber has an inlet opening and an outlet opening respectively at the level of parts of the wall which are situated opposite one another and form an edge of the measuring chamber in that part of the wall opposite the membrane which forms a ceiling of the measuring chamber, and the ceiling is drawn-in in a central area of the measuring chamber, so that a radial-channel-shaped part of the measuring chamber with a greater distance between the membrane and the ceiling and a central area of the measuring chamber with a smaller distance between the ceiling and the membrane are obtained, and the wall of the measuring chamber is designed such that it is free from any edges (rounded) with the exception of the inlet and outlet openings and the transition from the membrane to the remaining part of the wall.

This design, according to the invention, of a connecting element of the type mentioned at the beginning practically rules out the possibility of air bubbles remaining in the measuring chamber, even without for example knocking against the connecting element during filling with infusion solution. The filling without any air bubbles is achieved because the filling takes place from the infusion side to the catheter side in such a way that the long paths at the edge of the measuring chamber fill more quickly as a result of greater heights than the short path in the center. Furthermore, vortexing of the flow and the formation of gas-filled cavities are avoided on account of the surface tension of the fluid. In a way corresponding to this special shaping, the liquid flows meet when they emerge from the measuring chamber. With the previously customary dome-shaped shaping of the measuring chamber, air bubbles can remain in the sides, because the liquid flow blocks the simple escape of the air bubbles on the straight short path to the outlet.

In this case it is expedient if the annular-channel-shaped part of the measuring chamber is bounded on its outer circumference by the edge and connects the inlet opening to the outlet opening in such a way that it allows a flow to pass through.

In terms of fluid hydraulics, it is particularly advantageous if, in the central area, the ceiling is designed approximately in the form of a spherical cap. This applies correspondingly if the edge-free part of the wall has curvatures with a radius of at least one millimeter.

To obtain a good flow through the measuring chamber, with as little effect as possible on the measurement result, in spite of the low flow rates and the delivery being effected only by the higher hydrostatic pressure in comparison with the internal pressure inside the patient's body, it is advantageous if the inlet and outlet openings lie approximately in a plane parallel to the membrane, in particular if the distance of the plane in which the inlet and outlet openings lie from the membrane is not more than 3 mm.

For optimum filling, it has been found in tests to be advantageous if the flow-admitting cross section of the inlet opening is larger than the flow-admitting cross section of the outlet opening.

This applies in particular if the width of the inlet opening is at least 90% of the length of the inlet opening and/or the width of the outlet opening is no more than ⅔ of the length of the outlet opening.

To obtain a uniform transmission of the pressure waves in the entire frequency range of interest, it is advantageous if the flow-admitting cross section of the outlet channel has no sudden changes in cross-sectional area up to the outlet opening.

For use of the connecting element according to the invention in blood-carrying systems, for example in dialysis, it is particularly expedient if at least one inlet channel and/or at least one outlet channel is arranged inclined with respect to a plane parallel to the membrane, in particular if the inclination of the at least one inlet channel and/or of the at least one outlet channel with respect to a plane parallel to the membrane is approximately 15° to 45°, preferably 15° to 30°, particularly preferred approximately 20°. As a result, the forces on cells present in the fluid when it flows through the connecting element can be minimized. For example, a hemolysis, that is breaking up of the red blood corpuscles, can be avoided to the greatest extent.

In a commercially particularly advantageous embodiment, the connecting element according to the invention is characterized in that the connecting element comprises the membrane and a one-part plastics injection molding.

For visually checking that the measuring chamber is free from bubbles, it is advantageous if the connecting element comprises the membrane and a transparent plastics injection molding.

This object is further achieved according to the invention by a connecting element of the type mentioned at the beginning in which, in the region of the membrane, there is further provided a device for the mechanical coupling of the connecting element to the transducer and the device is part of a snap-on connection.

The design according to the invention also makes it possible even when there are hoses already connected to the connecting element for the connecting element to be connected to a transducer without turning movements, and in particular with only one hand, mechanically so securely that a satisfactory transmission of the pressures in the measuring chamber to the transducer, that is the pressure sensor, in the transducer housing to be [sic] ensured. Consequently, there is then also the possibility of designing retaining plates with a number of permanently fitted transducers and rear-side cabling. This produces a more simple and advantageous design with smooth fronts and, in particular, improved cable routing in the sense of more simple and reliable handling and hygiene, in particular in the area of intensive care.

For simplified handling, in particular in the case of complicated mounted structures of monitoring systems with a number of monitoring sets, it is expedient if the device for the detachable mechanical coupling of the connecting element is formed with the transducer.

In a particularly preferred embodiment of the invention, the spreading-in connection is formed by claw-shaped retaining elements for engagement in a corresponding groove or undercut of the transducer.

For simplest handling and secure seating, it is particularly advantageous if the claw-shaped retaining elements are resiliently connected to the housing, in particular if the claw-shaped retaining elements are formed by resilient continuations of the housing.

For particularly simple attachment and removal of such a connecting element according to the invention, it is advantageous if the claw-shaped retaining elements are at least partially connected to grips for actuating the retaining elements, in particular if the grips and associated retaining elements are formed in one piece.

An embodiment which is particularly appropriate for production is characterized in that pairs of retaining elements are formed in one piece with a grip, in particular if a total of four retaining elements arranged in a uniformly distributed manner are provided. In addition, this allows sterility of the entire connecting element together with the retaining elements to be established and maintained in a simple and reliable manner.

To avoid damage which could lead to a delay in mounting or dismantling a connecting element according to the invention, it is expedient if the resilient connection of retaining elements and grips with the housing is formed in such a way that no permanent damage to the resilient connection occurs when opposing grips are actuated to the extent that they touch one another. With corresponding dimensioning, blind attachment and removal of the connecting element with one hand is possible.

A particularly good compromise between material expenditure and ease of handling is obtained if the grips and retaining elements are dimensioned such that, when the grips are actuated, a ratio of approximately 2:1 to 3:1 between the path of the free ends of the grips and the path of the retaining elements is obtained.

The simplest attachment and removal of a connecting element according to the invention in the case of monitoring sets with a number of transducers on a retaining plate is obtained if the device for the mechanical coupling of the connecting element to the transducer is designed such that the connecting element can be mounted on the transducer in a direction approximately perpendicular to a plane which is defined by at least one inlet channel and at least one outlet channel.

BRIEF DESCRIPTION OF THE DRAWINGS

The invention is to be explained in more detail below on the basis of exemplary embodiments represented in the drawings, in which.

DESCRIPTION OF PREFERRED EMBODIMENTS OF THE INVENTION

Figure 3:
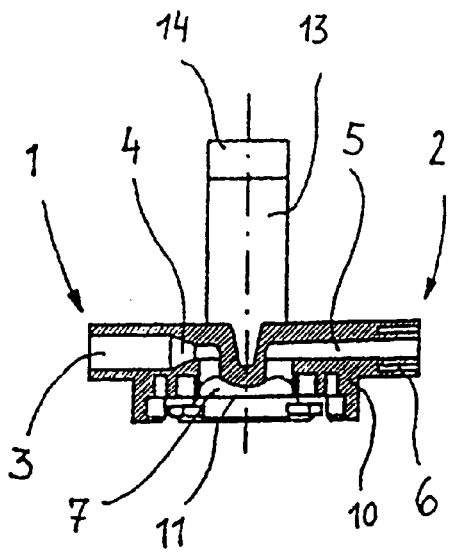
FIG. 3 shows the side view according to FIG. 1 in section.
Figure 1:
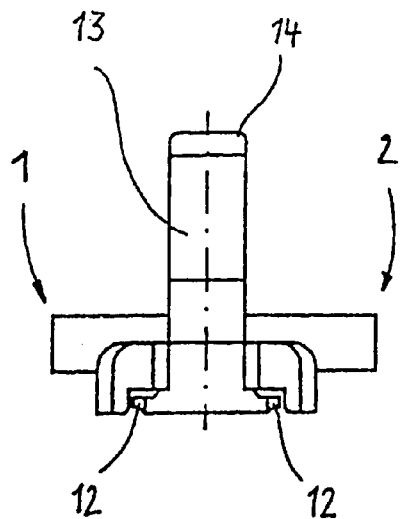
FIG. 1 shows a side view of a connecting element according to the invention.

The connecting element represented in FIG. 1 for connecting a transducer to a sealed fluid system has a connection 1 for the connection to an infusion apparatus and a connection 2 for the connection to a patient, for example via a cemented-in three-way cock. The connection 1 for the connection to an infusion apparatus has an inlet channel 3, preferably with a conical packing seat 4. The connection 2 for the connection to a patient contains an outlet channel 5 with a cementing-in groove 6 surrounding the latter (FIG. 3). The dimensioning of the connections 1 and 2 preferably conforms to DIN 13090.

Connected to the inlet channel 3 and the outlet channel 5 via an inlet opening 8 and an outlet opening 9 is a measuring chamber 7 (FIG. 4), so that a flow path from the inlet channel 3 through the measuring chamber 7 into the outlet channel 5 is obtained.

The measuring chamber 7 is formed in a housing 10 that [sic] is produced as a one-piece injection molding, preferably from a transparent plastic, for example a polycarbonate. Part of the wall of the measuring chamber 7 is formed by a flexible membrane 11 (omitted in FIG. 5), for example of a silicone material or some other suitable material that is resistant to the infusion, solution and is physiologically harmless. Consequently, the connecting part merely comprises the membrane 11 and a one-piece plastics injection molding.

In the region of the membrane 11 there is further provided a device for the mechanical coupling of the connecting element to the transducer which is part of a detachable spreading-in connection, which is formed by claw-shaped retaining elements in the form of hooks 12 for engagement in a corresponding groove or undercut of the transducer or an associated fastening device.

Figure 5:
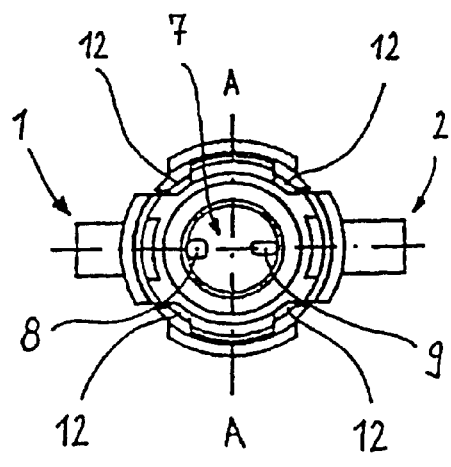
FIG. 5 shows a view from below of a connecting element according to the invention, represented without the membrane.
Figure 6:
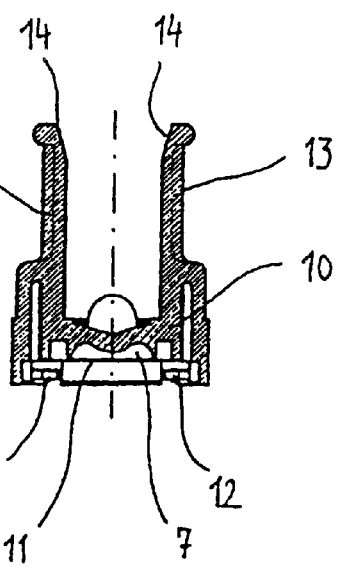
FIG. 6 shows a section through the connecting element according to the invention along the line A—A in FIG. 5.

The hooks 12 are formed by resilient continuations of the housing 10 and pairs of them are formed in one piece with a respective grip 13 in one piece [sic]. In this case, altogether four hooks 12 are provided, arranged in a uniformly distributed manner (FIG. 5). In this arrangement, the resilient connection of the hooks 12 and grips 13 to the housing 10 is designed such that, when the grips 13 are pressed together to the extent that they touch one another, no permanent damage to the resilient connection occurs (FIG. 6). Therefore, the connecting element can be mounted and dismantled blindly with one hand by pressing the grips 13 together in this way.

Figure 2:
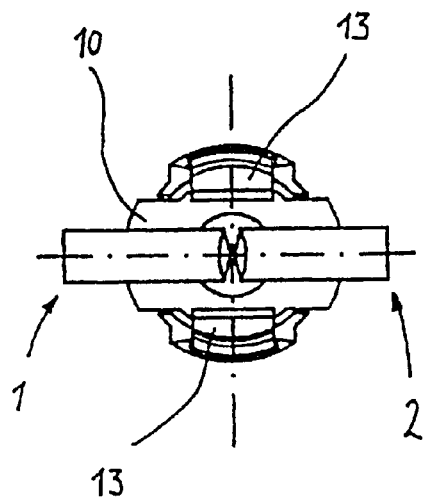
FIG. 2 shows a plan view of a connecting element according to the invention.

The grips 13 and hooks 12 are dimensioned such that, when the grips 13 are actuated, a ratio of approximately 2:1 to 3:1 between the path of the free ends 40 of the grips 13 and the path of the hooks 13 is obtained. As FIG. 2 clearly reveals, pressing the grips 13 together allows the connecting element to be mounted on the transducer in a direction approximately perpendicular to a plane which is defined by the inlet channel 3 and the outlet channel 5.

The measuring chamber 7 is bounded radially outward by part of its wall forming an edge 15, the inlet opening 8 and outlet opening 9 butting against this edge 15. In between and opposite the membrane 11, a ceiling 16 of the measuring chamber 7 is formed by part of the wall. The ceiling 16 is drawn-in in a central area 17 of the measuring chamber 7, so that an annular-channel-shaped part 18 of the measuring chamber 7 with a greater distance between the membrane 11 and ceiling 16 and a central area 17 of the measuring chamber 7 with a smaller distance between the ceiling 16 and membrane 11 is obtained.

In the central area 17, the ceiling 16 is advantageously designed approximately in the form of a spherical cap and the wall 15, 16 of the measuring chamber 7 is designed such that it is free from any edges (rounded) with the exception of the inlet and outlet openings 8, 9 and the transition from the membrane 11 to the remaining part of the wall, this rounding of the wall having curvatures with a radius of at least one millimeter.

Provided around the edge 15 there is also a groove 19. For fastening the membrane 11, a beaded edge (not represented) of the membrane 11 is pressed into the groove 19.

The inlet and outlet openings 8 and 9 lie approximately in a plane parallel to the membrane 11, the distance of the plane from the membrane preferably being no more than 3 mm. The flow cross section of the inlet opening 8 is greater than the flow cross section of the outlet opening 9. In this case, the width of the inlet opening 8 is at least 90% of the length of the inlet opening 8 and/or the width of the outlet opening 9 is no more than ⅔ of the length of the outlet opening 9. The cross-sectional areas of the inlet and outlet openings 8 and 9 each have radii of at least half a millimeter. To obtain a uniform transmission of the pressure waves in the entire frequency range of interest, the flow cross section of the outlet channel 5 has no sudden changes in cross-sectional area up to the outlet opening 9.

Figure 4:
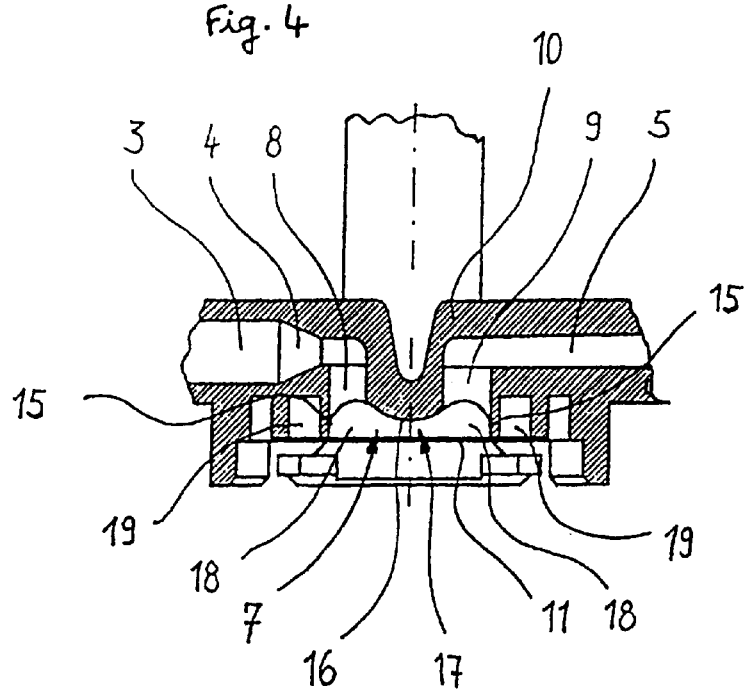
FIG. 4 shows an enlarged detail from the representation according to FIG. 3.
Figure 7:
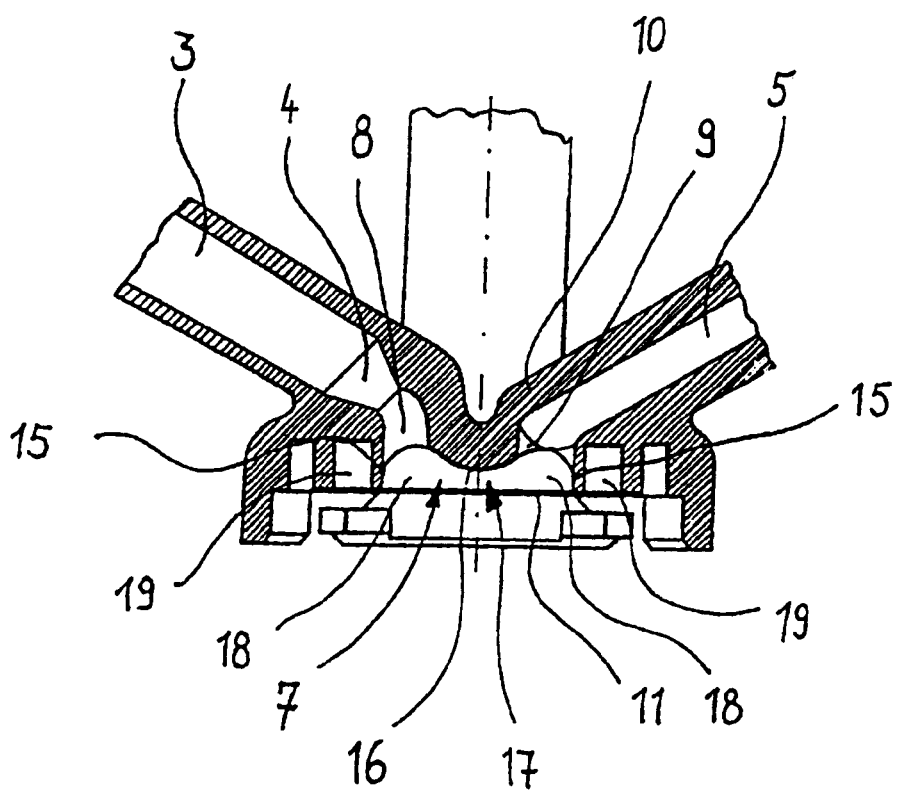
FIG. 7 shows a representation of a further embodiment of a connecting element according to the invention corresponding to the view in FIG. 4.

The representation in FIG. 7 corresponds to the representation in FIG. 4, but shows a further embodiment of the invention. For use of the connecting element according to the invention in blood-carrying systems, for example in dialysis, the inlet channel and/or the outlet channel 5 is arranged inclined with respect to a plane parallel to the membrane 11. It is advantageous in this case if the inclination of the inlet channel 3 and/or of the outlet channel 5 with respect to a plane parallel to the membrane 11 is approximately 15° to 45°, preferably 15° to 30°, particularly preferred approximately 20°. As a result, the forces on cells present in the fluid when it flows through the connecting element can be minimized. For example, a hemolysis, that is breaking up of the red blood corpuscles, can be avoided to the greatest extent.

What is claimed is:

1. A connecting element for connecting a transducer to a sealed fluid system, comprising at least one inlet channel, at least one outlet channel and a measuring chamber connected to said inlet channel and said outlet channel in such a way as to allow a flow to pass through said measuring chamber, the measuring chamber being formed in a housing and part of the wall of the measuring chamber being formed by a membrane which is significantly more compliant than the remaining part of the wall of the measuring chamber, wherein, in the region of the membrane, there is further provided a coupling device for the detachable mechanical coupling of the connecting element to a transducer, wherein the coupling device is part of a snap-on connection between said connecting element and said transducer, the coupling device for the mechanical coupling of the connecting element to a transducer is designed such that the connecting element can be mounted on the transducer in a direction approximately perpendicular to a plane which is defined by at least one of said inlet channels and at least one of said outlet channels.

2. A connecting element for connecting a transducer to a sealed fluid system, comprising at least one inlet channel, at least one outlet channel and a measuring chamber connected to said inlet channel and said outlet channel in such a way as to allow a flow to pass through said measuring chamber, the measuring chamber being formed in a housing and part of the wall of the measuring chamber being formed by a membrane which is significantly more compliant than the remaining part of the wall of the measuring chamber, wherein, in the region of the membrane, there is further provided a coupling device for the detachable mechanical coupling of the connecting element to a transducer, wherein the coupling device is part of a snap-on connection between said connecting element and said transducer, the coupling device comprises one or more claw-shaped retaining elements for engagement in a corresponding groove or undercut of a transducer, the claw-shaped retaining elements are at least partially connected to grips for actuating the retaining elements.

3. The connecting element as claimed in claim 2, wherein the grips and associated retaining elements are formed in one piece.

4. The connecting element as claimed in claim 3, wherein pairs of retaining elements are formed in one piece with a grip.

5. The connecting element as claimed in claim 2, wherein a total of four retaining elements arranged in a uniformly distributed manner are provided.

6. The connecting element as claimed in claim 2, wherein the resilient connection of retaining elements and grips with the housing is formed in such a way that no permanent damage to the resilient connection occurs when opposing grips are actuated to the extent that they touch one another.

7. The connecting element as claimed in claim 2, wherein the grips and retaining elements are dimensioned such that, when the grips are actuated, a ratio of approximately 2:1 to 3:1 between the path of the free ends of the grips and the path of the retaining elements is obtained.

* * * * *